United States Patent
Yamauchi

(10) Patent No.: US 8,093,059 B2
(45) Date of Patent: Jan. 10, 2012

(54) METHOD FOR SIMPLY QUANTITATIVELY DETERMINING HEXAVALENT CHROMIUM TECHNICAL FIELD

(75) Inventor: Yasuo Yamauchi, Shizuoka-ken (JP)

(73) Assignee: Yazaki Corporation, Tokyo (JP)

( * ) Notice: Subject to any disclaimer, the term of this patent is extended or adjusted under 35 U.S.C. 154(b) by 0 days.

(21) Appl. No.: 12/918,431

(22) PCT Filed: Feb. 16, 2009

(86) PCT No.: PCT/JP2009/052534
§ 371 (c)(1),
(2), (4) Date: Aug. 19, 2010

(87) PCT Pub. No.: WO2009/104551
PCT Pub. Date: Aug. 27, 2009

(65) Prior Publication Data
US 2011/0008898 A1    Jan. 13, 2011

(30) Foreign Application Priority Data

Feb. 21, 2008  (JP) ................................. 2008-040486

(51) Int. Cl.
*G01N 33/20* (2006.01)
(52) U.S. Cl. .............................. 436/83; 436/73; 436/169
(58) Field of Classification Search .................... 436/73, 436/83, 169
See application file for complete search history.

(56) References Cited

U.S. PATENT DOCUMENTS

| | | | | |
|---|---|---|---|---|
| 5,278,075 A | * | 1/1994 | Stone | 436/73 |
| 5,330,917 A | * | 7/1994 | Stone | 436/73 |
| 6,420,181 B1 | * | 7/2002 | Novak | 436/104 |
| 6,787,366 B1 | * | 9/2004 | Novak | 436/162 |

FOREIGN PATENT DOCUMENTS

| | | |
|---|---|---|
| JP | 10-332672 | 12/1998 |
| JP | 2003-172696 | 6/2003 |
| JP | 2006-322922 | 11/2006 |
| JP | 2007-139497 | 6/2007 |
| WO | WO 2007/047209 A2 | 4/2007 |

OTHER PUBLICATIONS

Office Action dated Nov. 26, 2010 in counterpart Portugal Application No. 2009104551.
Y. Yajima et al., "Determination of Chromium (VI) in Wasted Waters by Spot Test", Kogyo Yosui, No. 263, pp. 15-20 (1980).
A. Ishimaru, "Simple Determination of Hexavalent Chromium in Waste Liquid in Electrolytic Treatment", Kanagawa Industrial Technology Center Kenkyu Hokoku, No. 13, pp. 55-56 (2007).
International Search Report from the Japanese Patent Office dated Apr. 14, 2009, in PCT/JP2009/052534.

* cited by examiner

*Primary Examiner* — Robert J Hill, Jr.
*Assistant Examiner* — Dwan A Gerido
(74) *Attorney, Agent, or Firm* — Finnegan, Henderson, Farabow, Garrett & Dunner, L.L.P.

(57) ABSTRACT

Provided is a method for simply quantitatively determining hexavalent chromium, including: separately bringing a plurality of test solutions into contact with a sample, the plurality of test solutions each containing a color change agent which changes in color upon reaction with hexavalent chromium, and an acid which dissolves the sample, the plurality of test solutions having different contents of the acid from each other; detecting color change in each of the test solutions; and when the color change is detected, specifying a range of content of hexavalent chromium in the sample on the basis of the content of the acid in a test solution with the color changed among the plurality of test solutions.

2 Claims, 2 Drawing Sheets

| TEST SOLUTION | STANDARD SAMPLE [μg/cm²] | | |
|---|---|---|---|
| | 0.02 | 0.06 | 0.09 |
| STANDARD COMPOSITION PHOSPHORIC ACID:20ml | ○ | ○ | ○ |
| 0.375% PHOSPHORIC ACID:0.3ml | ○ | ○ | ○ |
| 0.0625% PHOSPHORIC ACID:0.05ml | × | ○ | ○ |
| 0.0375% PHOSPHORIC ACID:0.03ml | × | × | ○ |
| 0.00625% PHOSPHORIC ACID:0.005ml | × | × | × |

FIG. 1

| TEST SOLUTION | STANDARD SAMPLE [μg/cm²] | | |
|---|---|---|---|
| | 0.02 | 0.06 | 0.09 |
| STANDARD COMPOSITION PHOSPHORIC ACID:20ml | ○ | ○ | ○ |
| 0.375% PHOSPHORIC ACID:0.3ml | ○ | ○ | ○ |
| 0.0625% PHOSPHORIC ACID:0.05ml | × | ○ | ○ |
| 0.0375% PHOSPHORIC ACID:0.03ml | × | × | ○ |
| 0.00625% PHOSPHORIC ACID:0.005ml | × | × | × |

METHOD FOR SIMPLY QUANTITATIVELY DETERMINING HEXAVALENT CHROMIUM

TECHNICAL FIELD

The present invention relates to a simple hexavalent chromium quantitative determination method for simply quantitatively determining hexavalent chromium in a sample.

BACKGROUND ART

As a detection technique of hexavalent chromium, Patent Document 1 discloses a detector including an elution portion for eluting hexavalent chromium and a reaction portion which reacts with eluted hexavalent chromium. In the detector, the elution portion and the reaction portion are stacked on each other. The elution portion holds water and chemicals. The reaction portion contains a color change agent. When a sample comes into contact with a surface of the elution portion, the reaction portion changes in color. By detecting the color change, the presence or absence of hexavalent chromium in the sample is qualitatively measured. Patent Document 1: Japanese Patent Application Publication No. 2007-139497

SUMMARY OF INVENTION

Technical Problem

However, the above-described detector achieves merely a qualitative detection by which the presence or absence of hexavalent chromium in a sample is checked. Accordingly, the detector is incapable of performing a quantitative determination with which the content of hexavalent chromium in a sample is determined.

In this respect, an object of the present invention is to provide a simple hexavalent chromium quantitative determination method capable of simply determining a range of content of hexavalent chromium in a sample.

Solution To Problem

An aspect of the present invention is a method for simply quantitatively determining hexavalent chromium, the method comprising: separately bringing a plurality of test solutions into contact with a sample, the plurality of test solutions each containing a color change agent which changes in color upon reaction with hexavalent chromium, and an acid which dissolves the sample, the plurality of test solutions having different contents of the acid from each other; detecting color change in each of the test solutions; and when the color change is detected, specifying a range of content of hexavalent chromium in the sample on the basis of the content of the acid in a test solution with the color changed among the plurality of test solutions.

Advantageous Effects of Invention

The present invention can provide a simple hexavalent chromium quantitative determination method capable of specifying a range of content of hexavalent chromium in a sample in a simple manner.

BRIEF DESCRIPTION OF DRAWINGS

FIG. 1 is a table showing determination results of range of content of hexavalent chromium in an embodiment of the present invention.

DESCRIPTION OF EMBODIMENTS

Figure 2:
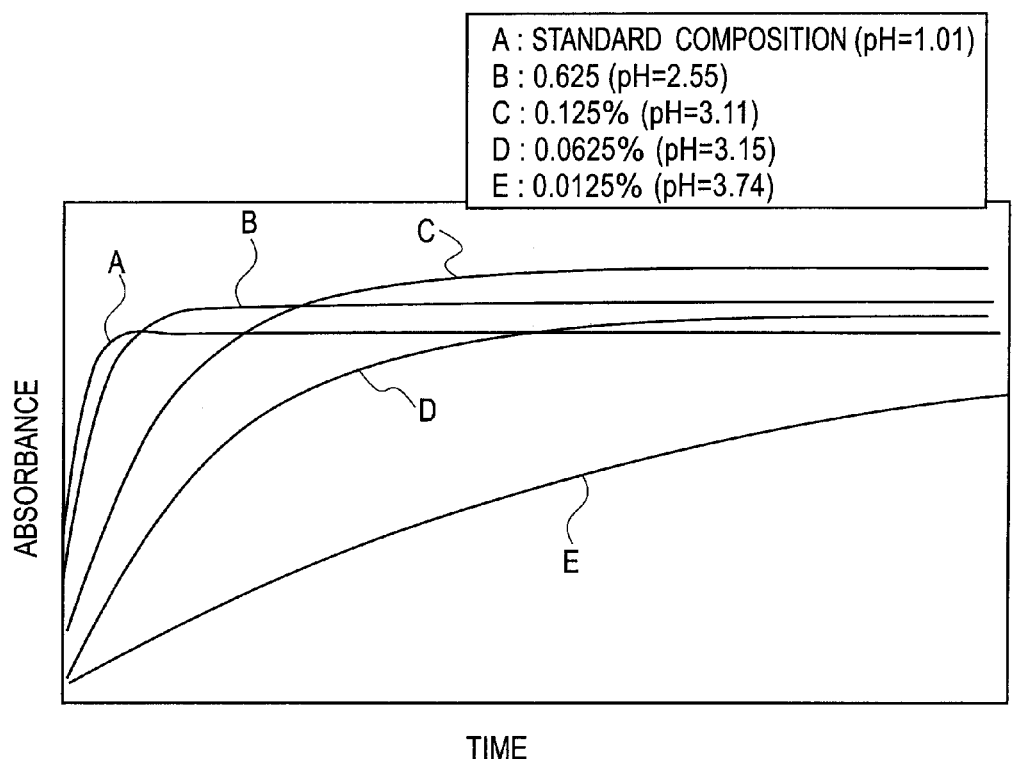
FIG. 2 is a graph showing change in absorbance with time.

Description will be given of a method for simply quantitatively determining hexavalent chromium according to an embodiment of the present invention.

In the method for simply quantitatively determining hexavalent chromium of this embodiment, multiple test solutions are prepared, each containing diphenylcarbazide and phosphoric acid. Diphenylcarbazide serves as a color change agent which changes in color upon reaction with hexavalent chromium, and phosphoric acid is an acid for dissolving a sample. The test solutions have different contents of phosphoric acid from each other. Next, the sample is brought into contact with each of the test solutions. Then, the presence or absence of color change in the test solutions is detected. On the basis of the detection results, the range of content of hexavalent chromium contained in the sample is specified.

(Sample)

A sample which uses iron (or an iron-based alloy) as a base material is used. Zinc-plating is formed on the base material for rust-prevention of iron. Further, a chemical conversion coating film is formed on the zinc-plating for rust-prevention thereof.

(Test Solutions)

Each of the test solutions contains diphenylcarbazide as the color change agent, acetone and ethanol as organic solvents, phosphoric acid as the acid, and water. The multiple test solutions are prepared as follows. Specifically, different amounts of phosphoric acid (0.3 ml, 0.05 ml, 0.03 ml, and 0.005 ml) are each mixed with a mixture liquid containing diphenylcarbazide (0.4 g), acetone (20 ml), and ethanol (20 ml). Then the total amounts are made identical (80 ml) by adding water. The solution into which 0.3 ml of phosphoric acid is blended is a test solution containing 0.375% of phosphoric acid in terms of volume concentration (hereinafter, the solution is referred to as a 0.375% test solution). Likewise, the test solution into which 0.05 ml of phosphoric acid is blended is referred to as a 0.0625% test solution, the test solution into which 0.03 ml of phosphoric acid is blended is referred to as a 0.0375% test solution, and the test solutions into which 0.005 ml of phosphoric acid is blended is referred to as a 0.00625% test solution. Note that, in the blending of each of the test solutions, diphenylcarbazide, acetone, ethanol, phosphoric acid, and water are blended in this order. In addition, the usable time of the test solutions are set to be 8 hours after the preparation (refer to ISO 3613).

(Standard Sample)

Standard samples to be used provide determination results of hexavalent chromium contents which are 0.02 μg/cm$^2$, 0.06 μg/cm$^2$, and 0.09 μg/cm$^2$, respectively. Here, the determination results are based on hot water extraction in which components in the coating film are taken out into hot water (boiling water) by immersing each of the samples in the hot water.

(Observation on Reaction of Test Solutions to Hexavalent Chromium)

When hexavalent chromium is contained in a sample, the hexavalent chromium reacts with diphenylcarbazide to form a chromium-diphenylcarbazone complex. The time required for the formation of this complex varies depending on the pH of a reaction solution. Specifically, a higher pH requires a longer time for the reaction. The pH of the reaction solution can be changed by changing the acid concentration. In addition, at a certain time point in a stage where the color change (color development) reaction is in progress, the intensities of color development differ between a reaction solution with a low pH and a reaction solution with a high pH. In other words, at a certain reaction time point, a state where color is developed and a state where no color is developed can be made depending on the difference in pH. On the basis of this fact, ability to detect hexavalent chromium can be changed by changing the acid concentration in the test solution.

In this respect, phosphoric acid is used to change the acid concentration. Specifically, the time required for the formation of the complex varies depending on the phosphoric acid concentration in the reaction solution. As is seen from determination results obtained by diphenylcarbazide absorption photometry shown in FIG. 2, the absorbance of the complex in an equilibrium state depends on the concentration of hexavalent chromium. In addition, the absorbance decreases as the phosphoric acid concentration deceases in the time period before the reach to the equilibrium state. This is because the time required until the equilibrium state is reached gets longer with the decrease in phosphoric acid concentration, leading to a slower reaction rate (refer to FIG. 2). Accordingly, by checking the color development before the color development reaction reaches the equilibrium state in the course of the reaction between the test solutions and the standard sample, the hexavalent chromium concentration at which the color development is observed can be identified based on the difference in reaction rate, and the detection sensitivity of hexavalent chromium can be adjusted.

On the basis of the above-described fact, the test solutions different from each other in phosphoric acid concentration were brought into contact with the standard samples. Thus the chromium-diphenylcarbazone complex was formed, and the color change in the test solutions was observed. Note that the color change in the test solutions is visually observed. There are various methods for the observation, such as a method in which each of the test solutions is placed dropwise on a surface of a sample, and the color development of the test solution on the surface of the sample is observed, a method in which each of the test solutions is placed dropwise on a surface of a sample, and only the test solution is transferred onto a watch glass for observation, and a method in which each of the test solutions is placed dropwise on a surface of a sample, then the test solution is blotted with a cotton swab, and the cotton swab is observed. In this embodiment, the surface of the sample was wiped with the cotton swab impregnated with the test solution, and the cotton swab was observed. The conditions for observation were as follows: the wiped area was set to 10±2 mm×4±1 mm, the number of times of wiping was set to two reciprocations, and the time to observation was set to 1 minute.

(Specifying of Range of Content of Hexavalent Chromium in Test Solutions Through Reaction)

FIG. 1 shows the determination results. Note that each "o" shown in the table indicates a test solution whose color change was visually observed, whereas each "x" indicates a test solution whose color change was not observed visually.

When a test solution having a standard composition employed generally and qualitatively (a solution obtained by blending 0.4 g of diphenylcarbazide, 20 ml of acetone, 20 ml of ethanol, 20 ml of phosphoric acid, and 20 ml of water with each other: refer to ISO 3613), the color change in the test solution was observed for all the standard samples. The color change in the 0.375% test solution having a phosphoric acid content of 0.3 ml was observed for all the standard samples. No color change in the 0.0625% test solution having a phosphoric acid content of 0.05 ml was observed for the standard sample having a hexavalent chromium content of 0.02 $\mu g/cm^2$. No color change in the 0.0375% test solution having a phosphoric acid content of 0.03 ml was observed for the standard samples having hexavalent chromium contents of 0.02 $\mu g/cm^2$ and 0.06 $\mu g/cm^2$, respectively. No color change in the 0.00625% test solution having a phosphoric acid content of 0.005 ml was observed for all the standard samples.

From the determination results, it can be understood that when the test solution having the standard composition does not change in color, the sample contains no hexavalent chromium. It can also be understood that when the test solution having the standard composition changes in color and when the 0.375% test solution does not change in color, the sample contains hexavalent chromium at 0 $\mu g/cm^2$ or more and less than 0.02 $\mu g/cm^2$. It can also be understood that when the 0.375% test solution changes in color and when the 0.0625% test solution does not change in color, the sample contains hexavalent chromium at 0.02 $\mu g/cm^2$ or more and less than 0.06 $\mu g/cm^2$. It can also be understood that when the 0.0625% test solution changes in color and when the 0.0375% test solution does not change in color, the sample contains hexavalent chromium at 0.06 $\mu g/cm^2$ or more and less than 0.09 $\mu g/cm^2$. It can also be understood that when the 0.0375% test solution changes in color, 0.09 $\mu g/cm^2$ or more of the hexavalent chromium is contained.

(Determination of Range of Content of Hexavalent Chromium in Sample)

First, the 0.375% test solution having the highest phosphoric acid content is brought into contact with a sample, and the color change in the test solution is observed. Next, when the test solution changes in color, the 0.0625% test solution having the second highest phosphoric acid content is brought into contact with the sample, and the color change in the test solution is observed. Similar operations are performed sequentially from the test solution having the highest phosphoric acid content to a test solution having a lower phosphoric acid content, until no color change in the test solution is observed.

As described above, by using the multiple test solutions different from each other in phosphoric acid content, the range of content of hexavalent chromium contained in a sample can be specified in a simple manner. Note that by using more test solutions different from each other in phosphoric acid content, the range of content of hexavalent chromium in a sample can be specified more specifically.

The method for simply quantitatively determining hexavalent chromium of the present invention makes it possible to specify the range of content of hexavalent chromium by bringing multiple test solutions different from each other in phosphoric acid content into contact with a sample. In this quantitative determination method, it is possible to easily detect how much hexavalent chromium is contained in a sample without employing a complicated operation. Accordingly, the range of content of hexavalent chromium in a sample can be determined in a simple manner.

Note that the number of the test solutions is four in the present invention, but the number is not limited thereto. When the number of test solutions different from each other in acid content is increased, the range of content of hexavalent chromium in a sample can be specified more precisely.

INDUSTRIAL APPLICABILITY

Without employing any complicated operation, the range of content of hexavalent chromium in a sample can be specified in a simple manner.

The invention claimed is:

1. A method for simply quantitatively determining hexavalent chromium comprising:

separately bringing a plurality of test solutions into contact with a sample, the plurality of test solutions each containing a color change agent which changes in color upon reaction with hexavalent chromium, and an acid which dissolves the sample, the plurality of test solutions having different contents of the acid from each other;

detecting color change in each of the test solutions; and when the color change is detected, specifying a range of content of hexavalent chromium in the sample on the basis of the content of the acid in a test solution with the color changed among the plurality of test solutions.

2. The method for simply quantitatively determining hexavalent chromium according to claim 1, wherein
the color change agent is diphenylcarbazide, and
the acid is phosphoric acid.

* * * * *